US006890738B2

(12) United States Patent
     Walker (10) Patent No.:     US 6,890,738 B2
(45) Date of Patent:     May 10, 2005

(54) PROLACTIN ANTAGONISTS AND USES THEREOF

(75) Inventor: Ameae Walker, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/065,330

(22) Filed: Apr. 23, 1998

(65) Prior Publication Data

US 2001/0036662 A1 Nov. 1, 2001

Related U.S. Application Data

(63) Continuation-in-part of application No. PCT/US97/01435, filed on Jan. 30, 1997, which is a continuation-in-part of application No. 08/594,809, filed on Jan. 31, 1996, now abandoned.

(51) Int. Cl.$^7$ ...................... A61K 38/22; C07K 14/575; C12N 15/16; C12N 15/63
(52) U.S. Cl. ................ 435/69.4; 435/320.1; 536/23.51; 514/2; 514/8; 514/12
(58) Field of Search .............................. 435/69.1, 69.4, 435/320.1, 243, 325; 536/23.1, 23.51; 514/2, 12, 8

(56) References Cited

U.S. PATENT DOCUMENTS

| 4,725,540 A | 2/1988 | Underberg et al. |
| 4,725,549 A | 2/1988 | Cooke et al. |
| 5,075,224 A | 12/1991 | Seeburg et al. |

OTHER PUBLICATIONS

Arámburo et al., "Phosphorylation of Prolactin and Growth Hormone," *Journal of Molecular Endocrinology*, 8, pp. 183–191 (1992).

Brooks et al., "Preparative Purification of Phosphorylated and Nonphosphorylated Bovine Prolactins," *Molecular and Cellular Endocrinology*, 99, pp. 301–305 (1994).

Clevenger et al., "Expression of Prolactin and Prolactin Receptor in Human Breast Carcinoma," *American Journal of Pathology*, 146 (3), pp. 695–705 (1995).

Cunningham et al., "Mediation of the Binding of Human Growth Hormone to Human Prolactin Receptor," *Science*, 250, pp. 1709–1712 (1990).

Fuh et al., "Mechanism–based Design of Prolactin Receptor Antagonists," *The Journal of Biological Chemistry*, 268, pp. 5376–5381 (1993).

Goffin et al., "Alanine–Scanning Mutagenesis of Human Prolactin: Importance of the 58–74 Region for Bioactivity," *Molecular Endocrinology*, 6(9), pp. 1381–1392 (1992).

Ho et al., "Secretion of Phosphorylated and Non–Phosphorylated Monomer Prolactin Isoforms During Rat Pregnancy and Pseudopregnancy," *Endocrine Journal*, 1, pp. 435–439 (1993).

Kim and Brooks, "Isolation and Characterization of Phosphorylated Bovine Prolactin," *Biochem J.*, 295, pp. 41–47 (1993).

(Continued)

*Primary Examiner*—Christine J. Saoud
(74) *Attorney, Agent, or Firm*—Ginger R. Dreger; James A. Fox; Heller Ehrman White & McAuliffe LLP (57) ABSTRACT

Recombinant nucleotide sequences encoding mutated prolactin are described. Expression of the sequences result in mimics of a phosphorylated prolactin corresponding to a selected species. A particularly preferred mimic is mutated at serine 179 (corresponding to human PRL) where serine is substituted by an aspartate residue. This aspartate mutant is a very effective antagonist and shows no ability to stimulate Nb2 to cell proliferation.

8 Claims, 3 Drawing Sheets

```
1   aac atg aac atc aaa gga tcg cca tgg aaa ggg tcc ctc ctg ctg ctg gtg tca aac
    N   M   N   I   K   G   S   P   W   K   G   S   L   L   L   L   V   S   N
61  ctg ctc ctg tgc cag agc gtg gcc ccc ttg ccc atc tgt ccc ggc ggg gct gcc cga tgc
    L   L   L   C   Q   S   V   A   P   L   P   I   C   P   G   G   A   A   R   C
121 cag gtg acc ctt cga gac ctg ttt gac cgc gcc gtc gtc ctg tcc cac tac atc cat aac
    Q   V   T   L   R   D   L   F   D   R   A   V   V   L   S   H   Y   I   H   N
181 ctc tcc tca gaa atg ttc agc gaa ttc gat aaa cgg tat acc cat ggc cgg ggg ttc att
    L   S   S   E   M   F   S   E   F   D   K   R   Y   T   H   G   R   G   F   I
241 acc aag gcc atc aac agc tgc cac act tct tcc ctt gcc acc ccc gaa gac aag gag caa
    T   K   A   I   N   S   C   H   T   S   S   L   A   T   P   E   D   K   E   Q
301 gcc caa cag atg aat caa aaa gac ttt ctg agc ctg ata gtc agc ata ttg cga tcc tgg
    A   Q   Q   M   N   Q   K   D   F   L   S   L   I   V   S   I   L   R   S   W
361 aat gag cct ctg tat cat ctg gtc acg gaa gta cgt ggt atg caa gaa gcc ccg gag gct
    N   E   P   L   Y   H   L   V   T   E   V   R   G   M   Q   E   A   P   E   A
421 atc cta tcc aaa gct gta gag att gag gag caa acc aaa cgg ctt cta gag ggc atg gag
    I   L   S   K   A   V   E   I   E   E   Q   T   K   R   L   L   E   G   M   E
481 ctg ata gtc agc cag gtt cat cct gaa acc aaa gaa aat gag atc tac cct gtc tgg tcg
    L   I   V   S   Q   V   H   P   E   T   K   E   N   E   I   Y   P   V   W   S
541 gga ctt cca tcc ctg cag atg gct gat gaa gag tct cgc ctt tct gct tat tat aac ctg
    G   L   P   S   L   Q   M   A   D   E   E   S   R   L   S   A   Y   Y   N   L
601 ctc cac tgc cta cgc agg gat nnn cat aaa atc gac aat tat ctc aag ctc ctg aag tgc
    L   H   C   L   R   R   D   X   H   K   I   D   N   Y   L   K   L   L   K   C
661 cga atc atc cac aac aac aac tgc taa gcc cac atc cat ttc atc tat ttc tga gaa ggt
    R   I   I   H   N   N   N   C   *   A   H   I   H   F   I   Y   F   *   E   G
721 cct taa tga tcc gtt cca ttg caa gct tct ttt agt tgt atc tct ttt gaa tcc atg ctt
    P   *   *   S   V   P   L   Q   A   S   F   S   C   I   S   F   E   S   M   L
781 ggg tgt aac agg tct cct ctt aaa aaa taa aaa ctg act cct tag aga cat c
    G   C   N   R   S   P   L   K   K   *   K   L   T   R   *   R   H
```

OTHER PUBLICATIONS

Luck et al., "Analysis of Disulphide Bridge Function in Recombinant Bovine Prolactin Using Site–Specific Mutagenesis and Renaturation Under Mild Alkaline Conditions: A Crucial Role for the Central Disulphide Bride in the Mitogenic Activity of the Hormone," *Protein Engineering*, *5*(6), pp. 559–567 (1992).

Luck et al., "Bioactive Recombinant Methionyl Bovine Prolactin: Structure–Function Studies Using Site–Specific Mutagenesis," *Molecular Endocrinology*, *3*(5), pp. 822–831 (1989).

Luck et al., "Single Amino Acid Substitutions in Recombinant Bocvine Prolactin that Markedly Reduce its Mitogenic Activity in Nb2 Cell Cultures, " *Molecular Endocrinology*, *5*(12), pp. 1880–1886 (1991).

Paris et al., "Bacterial Production and Purification of Recombinant Human Prolactin," *Biotechnology and Applied Biochemistry*, *12*, pp. 436–449 (1990).

Rhee et al., "Biological Activity and Immunological Reactivity of Human Prolactin Mutants," *Endocrinology*, *136*(11), pp. 4990–4995 (1995).

Walker, Ameae M., "Phosphorylated and Nonphosphorylated Prolactin Isoforms," *Trends Endocrinol. Metab.*, *5*, pp. 195–200 (1994).

Chen et al., "Development of a Recombinant Prolactin (PRL) Receptor Antagonist, "Abstract presented at the International Pituitary Congress 4th Satellite Meeting of the International Congress of Endocrinology, San Diego, California, Jun. 16–18, 1996.

Wang and Walker, "Dephosphorylation of Standard Prolactin Produces a More Biologically Active Molecule: Evidence for Antagonism between Nonphosphorylated and Phosphorylated Prolactin in the Stimulation of $Nb_2$ Cell Proliferation," *Endocrinology*, *133*(5), pp. 2156–2160 (1993).

Dialog Serach to Prolactin–, Antagonist– and Hyperprolactinemia, Jan. 1996.

Maciejewski et al., "Mutation of Serine 90 to Glutamic Acid Mimics Phosphorylation of Bovine Prolactin," *The Journal of Biological Chemistry*, *270*(46), pp. 27661–37665 (1995).

Goffin et al., "Evidence for a Second Receptor Beinding Site on Human Prolactin," *The Journal of Biological Chemistry*, *269*(51), pp. 32598–32606 (1994).

Chen et al., "Development of a Recombinant Human Prolactin Receptor Antagonists by molecular Mimicry of the Phosphorylated Hormone," *Endocrinology*, *139*(2), pp. 609–616 (1998).

Wang et al., "Identification of the Major Site of a Rat Prolactin Phosphorylation as Serin 177," *The Journal of Biological Chemistry*, *271*(5), pp. 2462–2469 (1996).

Oetting et al., "Phosphorylation of Prolactin," *The Journal of Biological Chemistry*, *261*, v. 4, pp. 1649–1652 (1986).

Greenan et al., "Biosynthesis of the Secreted 24K Isoforms of Prolactin," *Endocrinology*, *125*, v. 4, pp. 2041–2048 (1989).

Krown et al., "Prolactin Isoform 2 is an Autocrine Growth Factor for $GH_3$ Cells," *Endocrinology*, *131*, v. 2, pp. 595–602 (1992).

Ho et al, Secretion of Specific Nonphosphorylated and Phosphorylated Rat Prolactin Isoforms at Different Stages of the Estorous Cycle, *Neuroendocrinology*, *58*, pp. 160–165 (1993).

Lorenson et al., "Intragranular Prolactin Phosphorylation and Kallikrein Cleavage are Regulated by Zinc and Other Divalent Cations," *Endocrine*, *4*, v. 3, pp. 249–257 (1996).

```
  1 aac atg aac atc aaa gga tcg cca tgg aaa ggg tcc ctc ctg ctg ctg gtg tca aac
     N   M   N   I   K   G   S   P   W   K   G   S   L   L   L   L   V   S   N
 61 ctg ctc ctg tgc cag agc gtg gcc ccc ttg ccc atc tgt ccc ggc ggg gct gcc cga tgc
     L   L   L   C   Q   S   V   A   P   L   P   I   C   P   G   G   A   A   R   C
121 cag gtg acc ctt cga gac ctg ttt gac cgc gcc gtc gtc ctg tcc cac tac atc cat aac
     Q   V   T   L   R   D   L   F   D   R   A   V   V   L   S   H   Y   I   H   N
181 ctc tcc tca gaa atg ttc agc gaa ttc gat aaa cgg tat acc cat ggc cgg ggg ttc att
     L   S   S   E   M   F   S   E   F   D   K   R   Y   T   H   G   R   G   F   I
241 acc aag gcc atc aac agc tgc cac act tct tcc ctt gcc acc ccc gaa gac aag gag caa
     T   K   A   I   N   S   C   H   T   S   S   L   A   T   P   E   D   K   E   Q
301 gcc caa cag atg aat caa aaa gac ttt ctg agc ctg ata gtc agc ata ttg cga tcc tgg
     A   Q   Q   M   N   Q   K   D   F   L   S   L   I   V   S   I   L   R   S   W
361 aat gag cct ctg tat cat ctg gtc acg gaa gta cgt ggt atg caa gaa gcc ccg gag gct
     N   E   P   L   Y   H   L   V   T   E   V   R   G   M   Q   E   A   P   E   A
421 atc cta tcc aaa gct gta gag att gag gag caa acc aaa cgg ctt cta gag ggc atg gag
     I   L   S   K   A   V   E   I   E   E   Q   T   K   R   L   L   E   G   M   E
481 ctg ata gtc agc cag gtt cat cct gaa acc aaa gaa aat gag atc tac cct gtc tgg tcg
     L   I   V   S   Q   V   H   P   E   T   K   E   N   E   I   Y   P   V   W   S
541 gga ctt cca tcc ctg cag atg gct gat gaa gag tct cgc ctt tct gct tat tat aac ctg
     G   L   P   S   L   Q   M   A   D   E   E   S   R   L   S   A   Y   Y   N   L
601 ctc cac tgc cta cgc agg gat nnn cat aaa atc gac aat tat ctc aag ctc ctg aag tgc
     L   H   C   L   R   R   D   X   H   K   I   D   N   Y   L   K   L   L   K   C
661 cga atc atc cac aac aac aac tgc taa gcc cac atc cat ttc atc tat ttc tga gaa ggt
     R   I   I   H   N   N   N   C   *   A   H   I   H   F   I   Y   F   *   E   G
721 cct taa tga tcc gtt cca ttg caa gct tct ttt agt tgt atc tct ttt gaa tcc atg ctt
     P   *   *   S   V   P   L   Q   A   S   F   S   C   I   S   F   E   S   M   L
781 ggg tgt aac agg tct cct ctt aaa aaa taa aaa ctg act cct tag aga cat c
     G   C   N   R   S   P   L   K   K   *   K   L   T   R   *   R   H
```

PROLACTIN ANTAGONISTS AND USES THEREOF

The present application is a continuation of U.S. patent application Ser. No. 09/065,330, filed Apr. 23, 1998, which is a continuation-in-Part of PCT/US97/01435, WO 97/27865, filed Jan. 30, 1997, which is a continuation-in-part of U.S. application Ser. No. 08/594,809, filed Jan. 31, 1996 now abandoned. The entire texts of the above-referenced disclosures are specifically incorporated by reference herein.

The government owns rights in the present invention pursuant to grant number HD 28726 from the National Institutes of Health.

FIELD OF THE INVENTION

The present invention relates generally to the field of biologically active peptides and proteins that function as prolactin antagonists, and uses of these proteins/peptides in compositions for regulating prolactin and growth hormone related functions. More particularly, the invention concerns recombinant nucleotide sequences encoding a mutated prolactin, which is a mimic of human phosphorylated prolactin and is capable of antagonizing a prolactin receptor. The inventive mimic antagonizes the growth promoting effects of non-phosphorylated prolactin.

BACKGROUND OF THE INVENTION

Prolactin (PRL) is a polypeptide hormone produced by the anterior pituitary. This hormone is important in a number of physiological events, including maintaining normal reproductive functions, osmoregulation, growth, and immunoregulation.

Human prolactin has been characterized as a protein of 199 amino acids and as having a molecular weight of about 23 kDa. Prolactin from other species are reported to have a similar size, and to share a high degree of sequence homology.

For many years, PRL was considered an unmodified polypeptide hormone. It is now clear, however, that post-translational processing of PRL causes it to be phosphorylated, glycosylated and variously proteolytically cleaved. The phosphorylation of PRL within pituitary cells has also been demonstrated to occur in vivo in the rat, chicken, and cow. Phosphate analysis of purified preparations of PRLs from different species have demonstrated that prolactin from these species are variously phosphorylated with molar ratios of hormone to phosphate of 1.0:0.2 for bovine and rat and 1.0:0.7 for turkey.

Brooks et al., *Molecular and Cellular Endocrinology*, 99, pp. 301–305 (1994), have reported the isolation of a serine position 90 phosphorylated bovine prolactin species (position 90 relative to the naturally occurring amino acid sequence of bovine PRL), and examined the bioactivity of this molecule relative to native bovine prolactin. The native bovine prolactin was reported to be biologically active for stimulating cell proliferation in the Nb2 rat lymphoma bioassay used by those investigators, however, the serine 90 phosphorylated bovine prolactin was reported to be biologically inactive in the same bioassay.

Earlier functional studies have examined another phosphorylated prolactin species from the rat, this molecule being phosphorylated at serine residue 177. It was reported in that study that this mono-phosphorylated species of PRL (phosphoserine at position 177 of native rat prolactin amino acid sequence) acted as an antagonist to native, non-phosphorylated PRL in two cell systems (pituitary tumor cells, specifically GH3 cells that are PRL-producing rat pituitary tumor cell); and T lymphoma cells (Nb2 cell bioassay). Of significance, the serine 177 mono-phosphorylated-rat species of PRL was observed to act as an antagonist to non-phosphorylated prolactin, and to inhibit cell proliferation of Nb2 cells. Wang et al., *Endocrinology*, 133, pp. 2156–2160 (1993). The non-phosphorylated PRL was observed to promote cell proliferation of these prolactin dependent tumor cell lines. These observations stand in contrast to the lack of biological activity reported with the phosphorylated PRL species described in Brooks et al. (1994).

Native rat PRL is subject to ready phosphorylation in vivo. Those of skill in the art hold the view that these phosphorylated forms of PRL can be hydrolyzed by serum phosphatase to form non-phosphorylated prolactin, thus adding to the pool of non-phosphorylated PRL. As noted above, native, non-phosphorylated rat PRL has been reported to stimulate tumor cell growth. Thus, non-phosphorylated prolactin pools would be undesirable in the treatment of prolactin dependent tumors. This would render therapies with phosphorylated prolactin disadvantageous, as it may actually function to increase the proliferation of prolactin dependent tumors by supplying more of the prolactin species that binds prolactin receptor and turns on prolactin secretion and tumor growth. The half-life of phosphorylated prolactin is also relatively short, making it undesirable for use as a therapeutic. Recognition of this phenomenon makes the use of mono-phosphorylated PRL forms undesirable, as it may potentially worsen some conditions rather than provide a treatment.

U.S. Pat. No. 4,725,549, relates to a description of human and rat prolactin and preprolactin cloned genes. Paris et al., *Biotechnology & Applied Biochemistry*, 12, pp. 436–449 (1990) have described a recombinant human PRL that includes an additional methionine group at the amino terminal end of the molecule. These recombinant PRL species were observed to comigrate with human PRL on an SDS-polyacrylamide gel, and to have parallel dose response activity for stimulating Nb2 cell proliferation. The hPRL cDNA coding sequence reported by Cooke et al., *Journal of Biological Chemistry*, 256, pp. 4006–4016 (1981), and the T7 expression vector of Studier and Moffat, *Journal of Molecular Biology*, 189, pp. 113–130 (1986), was employed in preparing recombinant hPRL in a bacterial *E. coli* system. This technique provided a method for producing large quantities of recombinant non-phosphorylated PRL. However, a recombinant phosphorylated PRL, or a recombinant protein or peptide that mimics the prolactin antagonistic activity of phosphorylated PRL, has not before the present disclosure been described.

Abnormal levels of prolactin or abnormalities in the production of physiological concentrations of this hormone have been associated with several pathologies, including prolactin-dependent tumors. LHRH-like peptide prolactin antagonists have been proposed in the treatment of several specific pathologies, including hyperprolactinemia, miscarriage, precocious puberty and ovulation irregularities. For example, an LHRH C-terminal peptide has been described for use as a prolactin antagonist in the inhibition of prolactin-responsive tumors (U.S. Pat. No. 5,075,224).

A need continues to exist in the art for more stable and effective forms of non-LHRH like prolactin antagonists for therapeutic use. These molecules will preferably be capable of functioning as effective prolactin antagonists that compete with native prolactin for prolactin receptor sites, and which at the same time are not subject to dephosphorylation, thereby avoiding an increase in the pool of dephosphorylated prolactin. Such preparations could be used to control prolactin secretion and prolactin dependent tumor cell proliferation, as well as provide an improved treatment for other pathologies associated with abnormal prolactin regulation.

SUMMARY OF THE INVENTION

The present invention seeks to overcome the above and other drawbacks inherent in the prior art by providing stable molecules that are capable of functioning as prolactin antagonists without contributing to levels of dephosphorylated prolactin. The successful recombinant production of the prolactin antagonists described here offers the further advantage of large-scale production of these biologically active substituted prolactin proteins and peptides.

One aspect of the present invention pertains to human prolactin, which is phosphorylated at a serine residue 179. This phosphorylation site is important to the biological activity of the protein. This C-terminal region serine phosphorylation site is the major phosphorylation site. An identical phosphorylation site is present in all species. For example, in addition to humans, the serine is also conserved as serine 179 in whales, bovine, equine, ovine, and porcine species. Hence, the substitution proteins of this invention may be readily prepared to provide the biologically active molecules having prolactin antagonistic activity for virtually any species without undue experimentation, given the present disclosure, although human PRL is of particular interest.

Thus, the present invention provides a recombinant nucleotide sequence encoding a mutated prolactin. The expression of the sequence results in a mimic of a phosphorylated prolactin corresponding to a selected species. The mimic is capable of antagonizing growth promoting effects of non-phosphorylated prolactin in the selected species. The mimic is mutated at serine 179 (in the case of human and various other species) or its selected species equivalent. Prolactin mimics of this invention, particularly human phosphorylated prolactin mimics, are therapeutically useful such as in the treatment of prolactinoma, infertility related to abnormal prolactin regulation, some forms of prostatic cancer, ovulation irregularities, miscarriage, and other associated prolactin dependent disorders.

A particularly preferred prolactin mutant in accordance with the invention is wherein the mutated serine is substituted by an aspartate residue. This aspartate mutant is a very effective antagonist with 200 pg/ml negating 75% of the growth response to 400 pg/ml wild-type PRL. The aspartate mutant shows no ability to stimulate Nb2 cell proliferation.

The production of recombinant mimics in accordance with the invention can be relatively easily produced in large quantities and be entirely free of non-phosphorylated counterpart. The recombinant mimics cannot be dephosphorylated and thus cannot be converted to the growth-promoting form of PRL.

BRIEF DESCRIPTION OF THE DRAWINGS

FIG. 1 is the human substitution prolactin cDNA sequence (SEQ ID NO:1), and includes the signal sequence or pre-piece which is not present in the mature molecule, and corresponding substituted amino acid sequence (SEQ ID NO:2) still including the signal sequence. "X" at amino acid position 179 so-counted after the signal sequence is cleaved, is the serine 179 substitution in accordance with the invention and preferably is aspartate or glutamate, most preferably aspartate. The asterisks represent stop or nonsense codons present in the cDNA so that the "TAA"of the first asterisk terminates the prolactin at the preceding amino acid. The "NNN" located at nucleotide positions 622, 623 and 624 of SEQ ID NO:1 represent that encoding sequences for the substituted amino acids noted above.

DETAILED DESCRIPTION OF THE PREFERRED EMBODIMENTS

The primary site of PRL phosphorylation is serine 177 of the naturally occurring sequence of rat PRL and serine 179 of human PRL. Phosphorylation at this site has a major effect on the biological activity of the molecule, causing the phosphorylated PRL to become an antagonist to the non-phosphorylated hormone. Phosphorylation at this site can be duplicated by PKA and an intragranular PKA-like enzyme may be integral to the regulation of PRL structure and function in vivo. Substitution prolactin proteins and peptides that include other than phosphoserine at site 177 (rPRL) or site 179 (hPRL) have the potential for prolactin antagonistic activities, and to inhibit T-lymphoma cell proliferation. These substituted peptides/proteins thus present a new family of peptide/protein prolactin antagonists whose sequences are derived from the C-terminal fragment of prolactin that are not subject to dephosphorylation.

Figure 2:
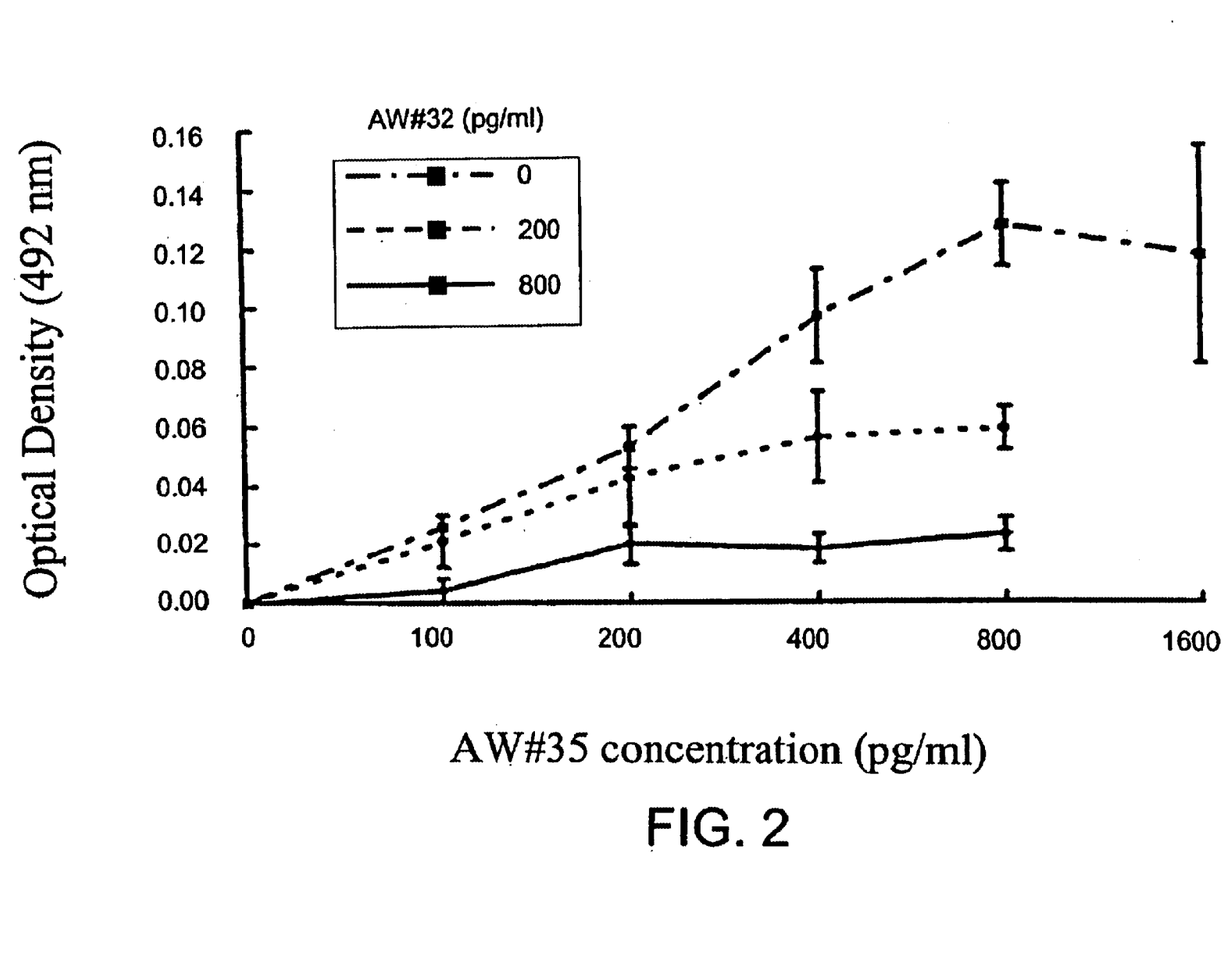
FIG. 2 graphically illustrates the results for the human glutamate mutant (AW 32) titrated against the recombinant wild type (AW 35) on the proliferation of T-lymphoma cells. Optical density at 492 nm is produced in the MTS assay and is a measure of cell number; and, FIG. 3 graphically illustrates the titration of aspartate mutant against wild-type PRL with Nb2 cells being plated at 1000/well and incubated in wild-type PRL with or without the addition of aspartate mutant at the concentrations indicated.
Figure 3:
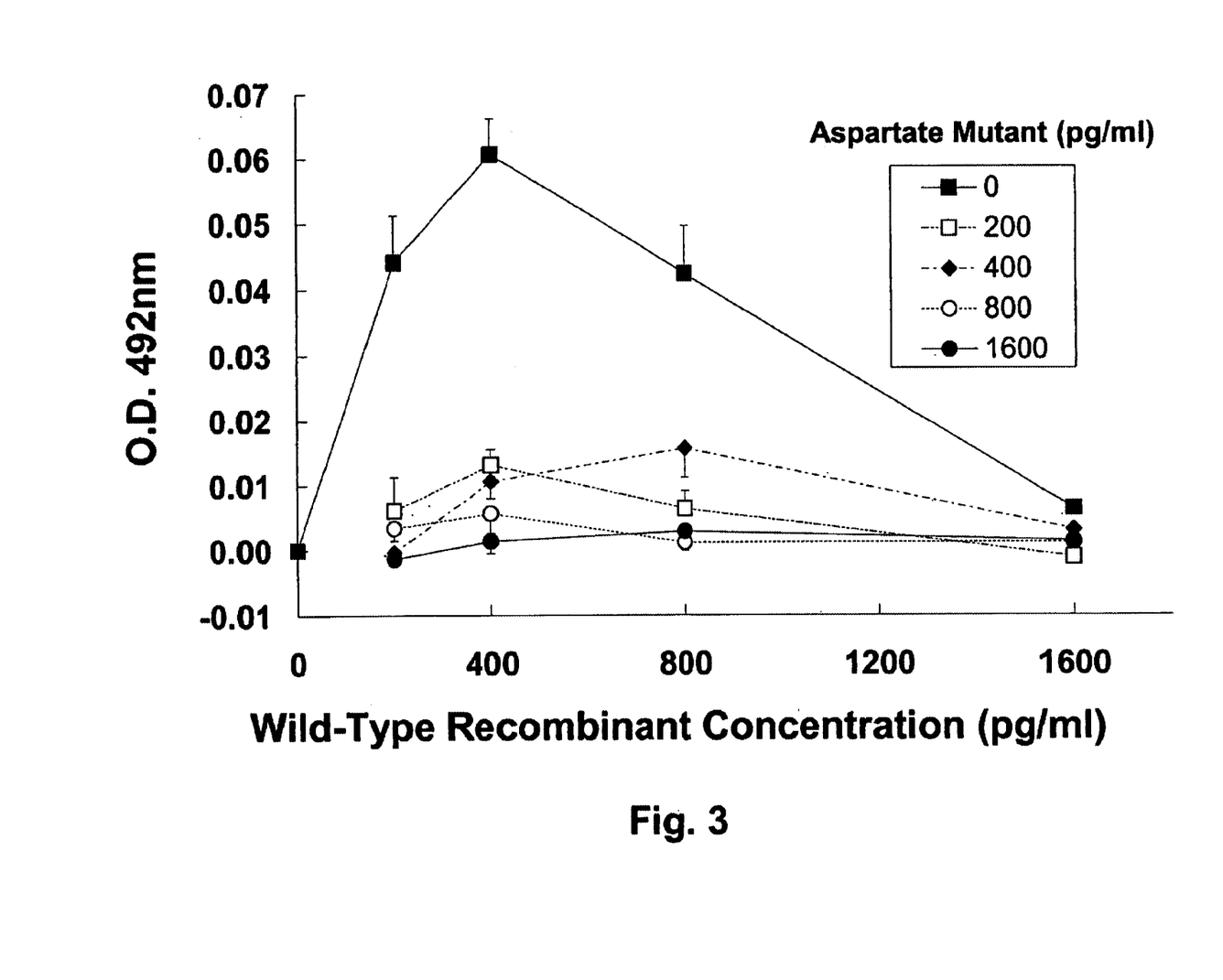

With reference to FIG. 1, when human prolactin cDNA is substituted so that the normal codon at nucleotide positions 622, 623, and 624 is replaced with other than those coding for serine indicated in SEQ ID NO:1 as "NNN", then such is a recombinant nucleotide sequence encoding a mutated prolactin. Preferred is where the serine mutation is by substitution with an aspartate or glutamate residue, particularly preferred where the serine mutation is by an aspartate residue substitution. With reference to FIG. 2, addition of 200 pg/ml of the glutamate mutant can reduce by half the growth response to 800 pg/ml of the wild type. The shape of the curves suggest non-competitive inhibition consistent with tighter binding of the glutamate mutant to receptor site 1. Mutation of the serine to valine or alanine, by contrast, produce molecules with no antagonist activity. With reference to FIG. 3, the aspartate mutant is a very effective antagonist with 200 pg/ml negating 75% of the growth response to 400 pg/ml wild-type PRL. Further, the aspartate mutant shows no ability to stimulate Nb2 cell proliferation.

The particularly identified substitution and monophosphorylated peptides of the invention are also described in conjunction with several particular methods of use. For example, these proteins and pharmaceutical compositions containing these proteins are useful in methods for modulating reproductive cycles, in the treatment of prolactin-dependent diseases and in the diagnosis of pathologies that are related to abnormal levels of prolactin, such as Parkinsonism.

Methods of using the compositions for managing lactation, such as to inhibit milk production in postpartum females, is also envisioned. The substituted prolactin proteins/peptides of the invention may thus be used either alone or in combination with bromocriptine and/or progesterone in regulating prolactin and lactation.

The designation of amino acid substitutions in some embodiments of the peptides and proteins of the invention relate to a substitution within the C-terminal end of the prolactin sequence. In specific embodiments, the substitution is located where serine is at position 177 (rat PRL) or serine position 179 of human PRL would occur in non-substituted prolactin. The serine residue that appears at residue number 177 in the rat sequence corresponds to the serine residue located at position #179 of the human sequence, to residue #177 in the mouse sequence, and to serine residue #179 of the bovine sequence.

While various of the amino acid residues in the C-terminal region of the non-phosphorylated, native prolactin encoding sequence have been examined for bioactivity, the criticality associated with substitutions of the serine residue in the creation of molecules that mimic the bioactivity of phosphorylated forms of prolactin had not previously been characterized, nor had the importance of the manipulation of this residue been appreciated or described in the creation of PRL antagonist substitution peptides and proteins as disclosed in the present invention.

The present invention also provides recombinant host cells and viral vectors comprising the substitution mutant sequences herein disclosed.

Expression vectors that comprise a nucleic acid molecule having a sequence operably linked to a promoter of DNA expression also constitute particular embodiments of the invention. The expression vector in one particular embodiment is PGEX3X, a pT7-7, or lambda gt11. Bacterial host cells comprising the aforedescribed expression vectors are also provided. By way of example, such bacterial hosts include JM109, XL-1-blue, or DH12S.

Expression of the substitution mutant proteins and peptides in a eukaryotic cell line are also provided in the present invention. The production of glycosylated forms of the mutant PRL proteins obtainable therefrom are envisioned as particularly useful for clinical application, glycoslated proteins possessing improved resistance to degradation. By way of example, such a cell line would be an insect cell line (e.g., SF9, ATCC #CRL1711 insect cell line using the expression vector, such as baculovirus (pAc700), or the CHO cell line such as that available at ATCC deposit #ATCC CRL 9606 or ATCC #10101, or ATCC 10154 with an expression vector such as pED, or pEE14.

Prokaryotic and eukaryotic hosts may be used for expression of the substitution proteins, peptides and analogs thereof. An example of a prokaryotic host which is particularly useful is *E. coli* strain BL21[DE3], M15[pREP4] and SG13009[pREP4]. *Enterobacteriaceae* species such as *Salmonella typhimurium* and *Serratia marcescens*, various *Pseudomonas* species, or gram-positive bacilli such as *Bacillus subtilus* may also be used.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using pBR322 (Bolivar et al., 1977), or one of its many derivatives. pBR322 contains genes which express ampicillin and tetracycline resistance in Gram-negative hosts and thus provides easy means for identifying transformed cells. pBR322, its derivatives, or other microbial plasmids or bacteriophage may also contain, or be modified to contain, promoters which can be used by the microbe for expression of endogenous proteins.

In addition, phage vectors containing replicon and control sequences that are compatible with the host microorganism can be used as transforming vectors in connection with these hosts. For example, bacteriophage such as lambda GEM-11n may be utilized in making a recombinant vector which can be used to transform susceptible host cells such as *E. coli* LE392.

Those promoters most commonly used in recombinant DNA construction include the β-lactamase (penicillinase) and lactose promoter systems (Change et al., 1978; Itakura et al., 1977; Goeddel et al., 1979) or the tryptophan (trp) promoter system (Goeddel et al., 1980; EPO Application Publication No. 0036776). While these are the most commonly used, other microbial promoters have been discovered and utilized, and details concerning their nucleotide sequences have been published, enabling a skilled worker to ligate them functionally with plasmid vectors (EPO Application Publication No. 0036776).

In addition to prokaryotes, eukaryotic microbes, such as yeast cultures may also be used. *Saccharomyces cerevisiae*, or common baker's yeast is the most commonly used among eukaryotic microorganisms, although a number of other strains are commonly available. For expression in *Saccharomyces*, the plasmid YRp7, for example, is commonly used (Stinchcomb et al., 1979; Kingsman et al., 1979; Tschemper et al., 1980). This plasmid already contains the trpL gene which provides a selection marker for a mutant strain of yeast lacking the ability to grow in tryptophan, for example ATCC No. 44076 or PEP4-1 (Jones, 1977). The presence of the trpL lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman et al., 1980) or other glycolytic enzymes (Hess et al., 1968; Holland et al., 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated in the expression vector 3' of the sequence desired to be expressed to provide polyadenylation of the mRNA and termination. Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, an origin of replication, and termination sequences is suitable.

In addition to microorganisms, cultures of cells derived from multicellular organisms may also be used as hosts. In principle, any such cell culture is workable, whether from vertebrate or invertebrate culture. However, interest has been greatest in vertebrate cells, and propagation of vertebrate cells in culture (tissue culture) has become a routine procedure in recent years. Examples of such useful host cell lines are VERO and HeLa cells, Chinese hamster ovary (CHO) cell lines, and W138, BHK, COS-7, 293 and MDCK cell lines. Expression vectors for such cells ordinarily include (if necessary) an origin of replication, a promoter located in front of the gene to be expressed, along with any necessary ribosome binding sites, RNA splice sites, polyadenylation site, and transcriptional terminator sequences.

For use in mammalian cells, the control functions on the expression vectors are often provided by viral material. For example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication (Fiers et al., 1978). Smaller or larger SV40 fragments may also be used, provided there is included the approximately 250 bp sequence extending from the HindIII site toward the Bg/I site located in the viral origin of replication. Further, it is also possible, and often desirable, to utilize promoter or control sequences normally associated with the desired gene sequence, provided such control sequences are compatible with the host cell systems.

The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

Recombinant host cells and recombinant vectors that incorporate an isolated DNA segment in accordance with the isolated DNA molecule as described above, are also disclosed. A particular recombinant vector that may be used is a PGEX3X which may be placed in JM109. Plasmids that include a sequence encoding the prolactin substitution peptide proteins are also described in the present disclosure. Any variety of different plasmids may used, such as, for example, the PGEM 11Zf(-) plasmid.

It is envisioned that the proteins (mimics) of the invention may be administered using those methods currently used to administer somatotropin (see Physicians Desk Reference; Goodman and Gilman's The Pharmacological Basis of Therapeutics, 8th edition (1990); (also see Rhemington's Pharmaceutical Sciences[38]; all of which are specifically incorporated herein by reference).

Lymphoma

By way of an example of a specific therapeutic formulation, the prolactin substituted proteins are envisioned as being particularly efficacious in the treatment of prolactin-responsive cancers, and particularly lymphomas. In these applications, it is proposed that the substituted proteins of the invention will be formulated as an injectable pharmaceutically acceptable formulation. The particular therapy to be given a patient will vary depending on the age, sex, weight and stage of the disease in the patient. A dosage in schedule of up to about 0.1 mg/kg administered 3 times a week, for example, intramuscularly or sub q, is one proposed regimen for the treatment of some forms of lymphoma. These dose ranges may vary, depending on the response of the patient to the treatment, and may be increased or decreased within a range of between about 8 mg/kg to about 40 mg/kg of a pharmaceutical preparation containing the substituted prolactin protein, depending on response of the patient.

Prolactinoma

By way of example, a normal adult human weighing about 70 kg, diagnosed as having a prolactinoma (which results in a hyperprolactinemic condition) or a pre-prolactinoma condition, could be treated with a pharmaceutically acceptable preparation of the aspartate recombinant substituted prolactin proteins described herein, preferably the human protein substituted protein forms. It is proposed that such a treatment would be administered intramuscularly or sub-q at a total dose of between about 14 mg/kg to about 35 mg/kg, so as to achieve an expected circulating level of the substituted protein of between about 90 ng/ml to about 200 ng/ml. serum in the patient.

Human patients with a prolactinoma, having a condition known as hyperprolactinemia, have been documented as having circulating levels of prolactin as high as 20 µg/ml serum. Based on these levels, it is proposed that the above dose ranges constitute reasonable ranges of the substituted prolactin as a prolactin antagonist in the treatment of this condition in the patient.

Pharmaceutical Preparations

The active compounds may only be orally administered, for example, with an inert diluent or with an assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of the active substituted prolactin protein or peptide compound. The percentage of the compositions and preparations may, of course, be varied and may conveniently be between about 2 to about 60% of the weight of the unit. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

The active compounds may also be administered parenterally or intraperitoneally. Solutions of the active compounds can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

It is also anticipated that the presently described monophosphorylated and substituted prolactin peptides/proteins may be formulated as a nasal spray, and used in therapeutically effective doses to treat the various prolactin-related disorders noted herein.

Sterile injectable solutions are prepared by incorporating the active compounds in the required amount in the appropriate solvent with various of the other ingredients enumerated above, as required, followed by filter sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

Antibodies

It is proposed that monoclonal antibodies of the present invention will find useful application in standard immunochemical procedures, such as ELISA and Western blot methods, as well as other procedures which may utilize antibody specific to the substituted prolactin epitopes. These substitution prolactin-specific monoclonal antibodies are anticipated to be useful in various ways for the detection of the relative levels of phosphorylated prolactin in a sample.

Additionally, it is proposed that monoclonal antibodies specific to the particular substituted prolactin may be utilized in other useful applications. For example, their use in immunoabsorbent protocols may be useful in purifying native or phosphorylated prolactin species or variants thereof.

In general, both poly- and monoclonal antibodies against the substituted prolactin, and hence the phosphorylated prolactin species, may be used in a variety of embodiments. For example, they may be employed in antibody cloning protocols to obtain cDNAs or genes encoding prolactin in different species or prolactin related proteins. They may also be used in inhibition studies to analyze the effects of phosphorylated prolactin in cells or animals. Anti-phosphorylated prolactin antibodies will also be useful in immunolocalization studies to analyze the distribution of this form of prolactin during various cellular events, for example, to determine the nuclear, OR cellular distribution during the presence or absence of a prolactin related diseased state. The operation of all such immunological techniques will be known to those of skill in the art in light of the present disclosure.

Epitopic Core Sequences-Identification of Additional Immunogenic Preparations

Further embodiments of the immunogen that may be used in preparing the antibodies of the present invention are thus contemplated to include protein compositions, free from total cells, characterized as having prolactin antagonist activity, that correspond to epitopic core sequences characteristic of the distinguishing prolactin substituted proteins and peptides of the invention. Preferred sources from which to isolate such proteins, include, but are not limited to, recombinant cells with eukaryote recombinant cells being the most preferred source. Such proteins may be produced by recombinant techniques following the molecular cloning of a DNA segment, as described herein.

The present invention is also directed to protein or peptide compositions, substantially free from mature forms of non-phosphorylated prolactin, which comprise a purified protein or peptide which incorporates an epitope that is immunologically cross-reactive with one or more of the substituted amino acid sequences as herein described.

As used herein, the term "incorporating an epitope(s) that is immunologically cross-reactive with one or more of the substituted amino acid sequences of Table 1" is intended to refer to a peptide or protein antigen which includes a primary, secondary or tertiary structure similar to an epitope located within one or more of the substituted sites in these substitution proteins. The level of similarity will generally be to such a degree that monoclonal or polyclonal antibodies directed against the substituted region of the mature protein will bind to, react with, or otherwise recognize, the cross-reactive peptide or protein antigen. Various immunoassay methods may be employed in conjunction with such antibodies, such as, for example, Western blotting, ELISA, RIA, and the like, all of which are known to those of skill in the art.

The identification of prolactin antagonist epitopes, and/or their functional equivalents is a relatively straightforward matter. For example, one may employ the methods of Hopp, as taught in U.S. Pat. No. 4,554,101, incorporated herein by reference, which teaches the identification and preparation of epitopes from amino acid sequences on the basis of hydrophilicity. The methods described in several other papers, and software programs based thereon, can also be used to identify epitopic core sequences, for example, Chou and Fasman, and Jameson and Wolf (Jameson & Wolf *Compu. Appl. Biosci.*, 4(1):181–6, 1988; Wolf et al. *Compu. Appl. Biosci.*, 4(1):187–91 1988) (Hopp, U.S. Pat. No. 4,554,101) (Kyte and Doolittle, 1982) address this subject. The amino acid sequence of these "epitopic core sequences" may then be readily incorporated into peptides, either through the application of peptide synthesis or recombinant technology.

Preferred peptides for use in accordance with the present invention will generally be on the order of 15 to 50 amino acids in length, and more preferably about 15 to about 30 amino acids in length. It is proposed that shorter antigenic peptides which incorporate epitopes of the various substituted prolactin proteins and peptides will provide advantages in certain circumstances, for example, in the preparation of vaccines or in immunologic detection assays.

An epitopic core sequence, as used herein, is a relatively short stretch of amino acids that is "complementary" to, and therefore will bind, antigen binding sites on antibodies. Additionally or alternatively, an epitopic core sequence is one that will elicit antibodies that are cross-reactive with substituted prolactin protein. It will be understood that in the context of the present disclosure, the term "complementary" refers to amino acids or peptides that exhibit an attractive force towards each other. Thus, certain epitope core sequences of the present invention may be operationally defined in terms of their ability to compete with or perhaps displace the binding of the desired protein antigen with the corresponding protein-directed antisera.

In general, the size of the polypeptide antigen is not believed to be particularly crucial, so long as it is at least large enough to carry the identified core sequence or sequences. The smallest useful core sequence anticipated by the present disclosure would generally be on the order of about 15 amino acids in length. Thus, this size will generally correspond to the smallest peptide antigens prepared in accordance with the invention. However, the size of the antigen may be larger where desired, so long as it contains a basic epitopic core sequence.

Syntheses of epitopic sequences, or peptides which include an antigenic epitope within their sequence, are readily achieved using conventional synthetic techniques such as the solid phase method (e.g., through the use of commercially available peptide synthesizer such as an Applied Biosystems Model 430A Peptide Synthesizer). Peptide antigens synthesized in this manner may then be aliquotted in predetermined amounts and stored in conventional manners, such as in aqueous solutions or, even more preferably, in a powder or lyophilized state pending use.

Storage

In general, due to the relative stability of peptides, they may be readily stored in aqueous solutions for fairly long periods of time if desired, e.g., up to six months or more, in virtually any aqueous solution without appreciable degradation or loss of antigenic activity. However, where extended aqueous storage is contemplated it will generally be desirable to include agents including buffers such as Tris or phosphate buffers to maintain a pH of 7.0 to 7.5. Moreover, it may be desirable to include agents which will inhibit microbial growth, such as sodium azide or merthiolate. For extended storage in an aqueous state it will be desirable to store the solutions at 4° C., or more preferably, frozen. Of course, where the peptide(s) are stored in a lyophilized or powdered state, they may be stored virtually indefinitely, e.g., in metered aliquots that may be rehydrated with a predetermined amount of water (preferably distilled) or buffer prior to use.

Clinical and Diagnostic Applications

Measurement of phosphorylated prolactin in a sample may be used as part of a clinical regimen in the management and prognosis of patients having or suspected as having, a prolactin-related disorder. Such disorders include, by way of example, a prolactin-dependent tumor, possibly prolactin related causes of infertility, prostatic cancers, mammary cancers and lymphomas.

The present invention concerns immunodetection methods and associated screening assays and kits for measuring phosphorylated prolactin, using the substituted prolactin proteins and peptides as target antigen in the production of antibodies. It is proposed that the substituted prolactin proteins or peptides of the present invention may be employed to detect antibodies having reactivity therewith, or, alternatively, antibodies prepared in accordance with the present invention, may be employed to detect levels of phosphorylated prolactin proteins or peptides. In general, these methods will include first obtaining a sample suspected of containing such a phosphorylated prolactin protein, peptide or antibody thereto, contacting the sample with an antibody or substituted prolactin protein or peptide in accordance with the present invention, as the case may be, under conditions effective to allow the formation of an immunocomplex, and then detecting the presence of the immunocomplex.

In general, the detection of immunocomplex formation is quite well known in the art and may be achieved through the application of numerous approaches. For example, the present invention contemplates the application of ELISA, RIA, immunoblot, dot blot, indirect immunofluorescence techniques and the like. Generally, immunocomplex formation will be detected through the use of a label, such as a radiolabel or an enzyme tag (such as alkaline phosphatase, horseradish peroxidase, or the like). Of course, one may find additional advantages through the use of a secondary binding ligand such as a second antibody or a biotin/avidin ligand binding arrangement, as is known in the art.

For diagnostic purposes, it is proposed that virtually any sample suspected of comprising either the phosphorylated prolactin protein or peptide or antibody sought to be detected, as the case may be, may be employed. Exemplary samples include clinical samples obtained from a patient such as blood or serum samples, ear swabs, sputum samples, middle ear fluid or even perhaps urine samples may be employed. Furthermore, it is contemplated that such embodiments may have application to non-clinical samples, such as in the titering of antigen or antibody samples, in the selection of hybridomas, and the like.

In related embodiments, the present invention contemplates the preparation of kits that may be employed to detect the presence of phosphorylated prolactin proteins or peptides and/or antibodies in a sample. Generally speaking, kits in accordance with the present invention will include a suitable substituted prolactin protein or peptide, or antibody directed against such a protein or peptide, together with an immunodetection reagent and a means for containing the antibody or antigen and reagent. The immunodetection reagent will typically comprise a label associated with the antibody or antigen, or associated with a secondary binding ligand. Exemplary ligands might include a secondary antibody directed against the first antibody or antigen or a biotin or avidin (or streptavidin) ligand having an associated label. Of course, as noted above, a number of exemplary labels are known in the art and all such labels may be employed in connection with the present invention.

The container will generally include a vial into which the antibody, antigen or detection reagent may be placed, and preferably suitably aliquotted. The kits of the present invention will also typically include a means for containing the antibody, antigen, and reagent containers in close confinement for commercial sale. Such containers may include injection or blow-molded plastic containers into which the desired vials are retained.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Following long-standing patent law convention, the terms "a" and "an" mean "one or more" when used in this application, including the claims.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Synthesis of Recombinant Rat PRL Substitution Peptides

This example outlines one method that may be used in the production of PRL substitution mutant recombinant peptides.

Materials and Methods

Production of Mutants

A pGEX-3X expression vector (Promega, Madison, Wis.) in which the glutathione S-transferase gene was linked to rat PRL cDNA was obtained from Dr. Mark Kelley (Department of Pediatrics, Indianapolis University, Bio Lab, Indianapolis, Ind. 46202). Digestion with Bam H1 and EcoR1 (1 μg plasmid DNA, 5 U Bam H1, 5 U EcoR1 in 20 μl of restriction buffer [50 mM NaCl, 10 mM Tris, 10 mM $MgCl_2$, 1 mM DTT, pH 7.9] at 37 C. for 40–60 min) isolated the PRL cDNA which was checked for appropriate size (approximately 600 base pairs) by electrophoresis in a 1% agarose gel in Tris acetate EDTA buffer (40 mM Tris-acetate, 2 mM EDTA, pH 8.5). The PRL cDNA fragment was then ligated into a pGEM 11Zf(-) plasmid (Promega). Ligation used 1 μg vector DNA, 200 ng insert DNA, 10 U of T4 DNA ligase in 10 μl of ligation buffer (30 mM Tris pH 7.8, 10 mM $MgCl_2$, 10 mM DTT, 1 mM ATP) at 16° C. for 8 h. This pGEM recombinant was then transfected into the E. coli strain CJ236 by electroporation at 1.25 KV/mm in a BTX electroporation system (San Diego, Calif.) (clone AW #4). The clone then grew in LB broth (1% Tryptone, 0.5% yeast extract, 1% NaCl, pH 7) with uridine (0.25 μg/ml). This E. coli strain produces dU-containing single stranded DNA in the presence of helper phage M13K07.

Serine 177 mutation was achieved with an oligonucleotide 23 mer with the sequence GCAGGGAT<u>GAC</u>CACAAGGTTGAC (SEQ ID NO:3) (plus(+) strand primer) in which GAC (underlined) replaces the TCC of serine 177. Other substituted primers may be prepared as well, where the GAC (aspartate) is replaced with a codon sequence that encodes aspartate, or that encodes amino acid glutamate, tyrosine, alanine, tryptophan or histidine. A more generic primer that describes these nucleic acid substitutes is as follows:

5' CGCAGGGAT<u>GNA</u>CACAAGGTTGA 3' (SEQ ID NO:4)

This primer will result in a mutation at serine 177, rPRL, wherein GNA substitution represents the four possible amino acid substitutions (valine, glutamate, alanine and glycine). Worst duplex formation was estimated at -4.4 kcal/mol and hairpin ΔG at 0.1 kcal/mol. Phosphorylation of this oligonucleotide was produced by T4 polynucleotide kinase (200 pmol primer, 5 U T4 kinase, 0.4 mM ATP in 20 μl kinase buffer [50 mM Tris, pH 7.5, 10 mM $MgCl_2$, 5 mM DTT, 0.1 mM spermidine] at 37° C. for 45 min) and the reaction was stopped by incubation at 65° C. for 10 min.

Single-stranded DNA was prepared by precipitation from the culture medium with a final concentration of 4% polyethylene glycol in 0.5 M NaCl. After resuspension in Tris-EDTA (20 mM Tris, 1 mM EDTA, pH 7.5) single-stranded DNA was extracted with phenol/chloroform (once) and chloroform (twice), and then precipitated by ethanol.

dU-containing single-stranded DNA was annealed to the phosphorylated oligo primer. 10 pmol oligomer per 200 ng dU-single-stranded DNA in 10 μl annealing buffer (20 mM tris, pH 7.4, 2 mM $MgCl_2$, 50 mM NaCl) were incubated first at 70° C. for 5 min, then at 37° C. for 30 min, then at room temperature for 5 min and then on ice. Double-stranded DNA was produced by incubation in 3 U of T4 ligase, 0.5 U T7 DNA polymerase (Bio-Rad) in synthesis buffer (0.5 mM dNTP, 1 mM ATP, 20 mM Tris, pH 7.4, 4 mM $MgCl_2$, 0.5 mM DTT) first on ice for 5 min followed by incubation at room temperature for 5 min and 37° C. for 90 min.

The resultant double-stranded DNA was transfected into the JM109 E. coli strain in which the dU strand was destroyed and the mutant strand repaired and retained. Two of twelve clones analyzed by sequencing had the mutation (clone AW #5). The mutant DNA was excised as above and placed back into the original pGEX-3X expression vector (clone AW #8). To ensure equal treatment of the non-mutated PRL cDNA, the original rat PRL expression construct was also placed in JM109 clone (AW #7).

Expression and Purification of Recombinant Wild-type and Mutant PRLs

AW#7 (for wild-type PRL) or AW#8 (for mutant PRL) cells were cultured in 2× yeast tryptone broth (1.6% Tryptone, 0.5% NaCl, 1% yeast extract, pH 7) with ampicillin (50 μl/ml) overnight at 37° C. The overnight culture (10 ml) was diluted 10 times in the same medium and incubated at 37° C. with vigorous agitation for 1.5 h. Isopropyl β-thiogalactosidase (final concentration 0.1 mM) was added to the culture to induce expression of the fusion protein and incubation was continued for another 2 h. The bacteria in the liquid culture were pelleted and resuspended in 20 ml ice-cold 0.01 M PBS. The bacteria were lysed using a Micro-Ultrasonic cell disrupter (3×30 sec. at setting 7) and then centrifuged at 14,000×g for 10 min. The pellet was resuspended in 8 ml 0.1 M glycine-NaOH (pH 9.0) with 8 M urea and incubated on ice for 10 min. After centrifugation (14,000×g, 5 min) to remove insoluble material, the supernatant was dialyzed against 4×4l 0.1 M glycine-NaOH (pH 9.0), 16 h at 4° C. to remove urea, meanwhile, allowing the fusion protein to refold. A 0.5 ml aliquot of the recovered protein solution was diluted to 3.0 ml with TBS (50 mM Tris with 150 mM NaCl, pH 7.4) and added to 0.5 ml of preequilibrated glutathione-agarose gel (Sigma). The slurry was gently mixed for 30 min at room temperature, subjected to centrifugation at 1,000×g for 5 min and the supernatant discarded. After washing five times with 5 ml TBS, the fusion protein was eluted with 1 ml of 10 mM glutathione in 50 mM Tris (pH 7.4). The amount of purified fusion protein was determined by reference to several standard amounts of PRL and glutathione S-transferase and mol wt. markers co-run in a 12% SDS-PAGE system, stained with Coomassie blue. The fusion protein was digested with Factor Xa (Pierce) at an enzyme to substrate wt:wt ratio of 1:50. A 20 fold concentrated digestion buffer was added to the solution to give a final concentration of 50 mM Tris, 100 mM NaCl, 6 mM $CaCl_2$, pH 8.0, and the digestion mixture was incubated at 37° C. for 2 h. The cleaved protein solution was dialyzed against 4×1 l 50 mM Tris (pH 7.4), 16 h at 4° C. to remove glutathione. After dialysis, concentrated NaCl was added to the solution to give a final concentration of 150 mM and this was mixed with 0.5 ml glutathione-agarose gel for 30 min at room temperature. The gel was pelleted by centrifugation and the supernatant was collected. The purity and quantity of the recombinant PRL was again determined by reference to standard rat PRL B7 co run in a 12% SDS-PAGE system. Quantification was achieved using a CCD camera and NIH imaging software.

The biological activity was assessed as described in Example 2.

EXAMPLE 2

Biological Activity of Rat PRL Substitution Peptide; Inhibition of Nb2 Lymphoma Cell Proliferation This example demonstrates the activity of the substitution rat prolactin peptides, particularly for the inhibition of prolactin-dependent tumor cell proliferation.

The Nb2 bioassay was performed as follows. Briefly, Nb2 T-lymphoma cells were maintained in Fisher's medium containing 10% fetal bovine serum (FBS), 10% horse serum (HS), $10^{-4}$ M $NaHCO_3$, $10^{-4}$ M β-mercaptoethanol and penicillin (20 U/ml)/streptomycin (20 μg/ml). Before the bioassay, cells were transferred to 1% FBS-10% HS medium for 24 h. The cells were then plated in 96-well plates with 5,000 cells/200 μl of Fishers medium containing 10% HS and no FBS/well. Different concentrations and combinations of rat PRL-B-7, standard human prolactin recombinant wild-type and mutant PRL were added to the wells in quadruplicate.

After 3 days of culture, cell number in each well was measured using an MTS assay which is a slight modification of the MTT method previously described. Briefly, MTS dye, 3-(4,5-dimethylthiazol-2-yl)-5-(3-carboxymethoxyphenyl)-2-(4-sulfophenyl)-2H-tetrazolium (Promega, 2 mg/ml in Dulbecco's phosphate buffered saline, DPBS) was mixed with phenazine methosultate (Sigma. 0.92 mg/ml DPBS) at a ratio of 20:1 (by volume). The mixture (20 μl) was added to each well (200 μl) and the plate was incubated at 37 C for 2 h. The cells were lysed by adding 20 μl/well of 10% SDS and absorbance of the medium at 492 nm was determined in an EIA plate reader (Bio-Rad, Richmond, Calif.).

It is important to note that the pseudophosphorylated PRL has no Nb2 biological activity of its own. Titration of the pseudophosphorylated PRL against the recombinant non-phosphorylated PRL shows the pseudophosphorylated PRL, like naturally phosphorylated PRL, to act as an antagonist to Nb2 cell proliferation. When titrated at ⅓ the amount of non-phosphorylated material, it inhibits proliferation by about ⅓.

EXAMPLE 3

Mutants of Human PRL; Subcloning and Site-directed Mutagenesis

The hPRL complementary DNA clone (pBR-hPRL) was obtained from the American Type Culture Collection (Rockville, Md.). A 686-bp PpuMI fragment, which contained the full hPRL-coding region, was subcloned into the SmaI site of pUC118 (U.S. Biochemical Corp., Cleveland, Ohio) in which the BamHI site was nullified. This recombinant was transformed into *Escherichia coli* CJ236 cells, which produce dU-containing single-stranded DNA after infection with M13K07 helper phage and incubation of 0.25 μg/ml uridine.

Site directed mutagenesis was performed using a Muta-Gene in vitro mutagenesis kit (Bio-Rad, Hercules, Calif.). One primer (ACGCAGGGATGNKATAAAATCG, SEQ ID NO:5) was designed to substitute serine 179 with glutamate, aspartate, alanine, or valine. A second primer (CGTGGCCCCCATATGTTGCCCATCTG, SEQ ID NO:6) was used to facilitate cloning into an expression vector via the production of an NdeI site. Appropriate mutations were confirmed by sequencing. Mutated DNA was subcloned into pT7-SCII (U.S. Biochemical Corp.), which was placed into *E. coli* BL21 (DE3) for protein expression.

Protein Expression

Cells were cultured in Lura Bertoni broth with ampicillin (200 μg/ml) overnight at 37° C. The overnight culture was diluted 10 times in the same medium, aliquoted into 3-ml amounts, and incubated at 37° C. with agitation until the OD 600 nm reached 0.55–0.6. Isopropyl β-thiogalactoside (final concentration, 0.5 mM) was added to the culture to induce expression of the protein. Optimizing experiments determined that the best yield coupled to the best purity was obtained after a 2-h induction. The bacteria (3 ml) were pelleted and resuspended in 500 μl ice-cold 50 mM Tris-HCl pH 7.5. They were then lysed using a MicroUltrasonic cell disrupter (five 15-sec pulses at setting 9 on ice, with a 30-sec pause between pulses) and then centrifuged at 14,000×g for 10 min at 4° C.

Expressed PRLs were primarily in inclusion bodies that formed the 14,000×g pellet. After washing in ice-cold 50 mM Tris-HCl pH 7.5, they were denatured in 8 M urea-1% β-mercaptoethanol in 0.2 M sodium phosphate, pH 7, and the resulting solution was dialyzed against 20 vol 50 mM $NH_4HCO_3$, with eight changes in 3 days at 4° C., with a final protein concentration of 0.1 mg/ml.

The amount of protein present was determined either by quantitative gel densitometry by comparison to hPRL standards or by using the NanoOrange kit (Molecular Probes, Eugene, Ore.). In the latter instance, NIDDK hPRL B-3 was dissolved in 50 mM $NH_4HCO_3$ and serially diluted to produce the reference standard curve. Both methods gave comparable results. Highly purified BSA (Sigma Chemical Co., St. Louis, Mo.) was added (to 0.05%) as soon as possible to reduce recombinant protein losses caused by adherence or proteolysis.

RIA Analysis of the Recombinant PRLs

Recognition of the mutual PRLs compared with two standard NIDDK PRLs, hPRL I-8 and rPRL B7, in a commercially available RIA was used as a measure of appropriate folding. Each protein was dissolved first in 50 mM $NH_4HCO_3$, accurately quantified and then diluted in the 0 calibrator provided with the kit. The kit was purchased from Diagnostic Products Corp. (Los Angeles, Calif.).

Endotoxin Analysis of the Preparations

Endotoxin contamination of the PRLs was first tested using the E-TOXATE kit from Sigma and by gel analysis for bacterial lysate endotoxins. Briefly, for the latter, proteinase K-deproteinated samples were run on a 14% SDS reducing polyacrylamide gel and then silver stained to detect endotoxin bands.

Preparations were also tested for toxicity at concentrations up to 0.5 μg/ml by analyzing changes in cell proliferation over a 72-h period in bone SaOs cells (American Type Culture Collection).

In addition, parallel preparations of the various mutants and the wild-type PRL were made so that on each occasion the wild-type PRL could be analyzed for biological activity relative to those of the other preparations as well as to those of NIDDK standards in the Nb2 bioassay.

Dephosphorylation of Standard hPRL

Standard hPRL I-8 was exposed to acid phosphatase (from human semen; Sigma) at a ratio of 10 μg to 1 U enzyme in 0.1 M sodium citrate buffer, pH 5, for 2 h at 37° C. Control aliquots of the hormone alone and enzyme alone were incubated in buffer for the same period and at the same temperature. After 2 h of incubation, the samples were diluted 40-fold in Dulbecco's PBS (DPBS) containing 0.1%

BSA (highly purified from Sigma). Each sample (enzyme-treated, buffer-incubated, and enzyme in buffer) was sterilized by filtration and stored frozen at −20° C. until further dilution in 0% FBS-10% horse serum (HS)-Nb2 assay medium.

Biological Activity of the Wild-type, Mutant PRLs and Dephosphorylated NIDDK Standard PRL Briefly, Nb2 T lymphoma cells (originally obtained from Henry Fries, now at Medical Research Council, Ottawa, Canada) were maintained in Fisher's medium containing 10% FBS, 10% HS, 0.1 nM NaHCO$_3$, 0.1 nM β-mercaptoethanol, and penicillin (20 U/ml)/streptomycin (20 μg/ml). Before the assay, cells were transferred to 1% FBS-10% HS medium overnight. The cells were then plated onto 96-well plates in 100 μl (1%) FBS-10% HS medium/well. Different concentrations and combinations of PRLs, diluted in 0% FBS-10% HS medium, were added to give a total volume of 200 μl/well. For measurement of proliferation, 5000 cells/well were used. For studies of antagonism, 1000 cells/well were used to increase competition for the receptors. The number of cells required to produce receptor-limiting conditions during a 3-day incubation was determined empirically. In each experiment (5000 or 1000 cells/wells) the response to wild-type PRL alone was used as a positive control and a measure of comparability among experiments. Cell number was assessed 72 h after plating using an MTS assay (1, 11). Briefly, MTS dye [3(4,5-dimethylthiazol-2-yl)-5(3-carboxymethoxyphenyl)-2-(4-sulfophenyl)-2H-tetrazolin, Promega Corp., Madison, Wis.] at 2 mg/ml in DPB was mixed with phenazine methosulfate (Sigma; 0.92 mg/ml DPBS) at a ratio of 20:1 (vol/vol). Twenty microliters of the mixture were then added to the 200 μl medium in each well, and the plate was incubated for 2 h at 37° C. before reading the absorbance at 492 nm in an enzyme immunoassay plate reader (Bio-Rad). Results were expressed as the absorbance in the test wells minus the absorbance in the wells containing cells but no added PRL.

Within each assay, each test substance, combination, or amount was assayed in quadruplicate. Each assay result was replicated at least twice with each preparation of protein, and each result was replicated with at least two, and in most instances three, separate preparations of protein.

Biological Activity

The recombinant wild-type PRL had greater biological activity in the Nb2 bioassay than did the NIDDK hPRL B-3 preparation. This result attests to (1) the absence, or very low levels, of endotoxin in the preparation; and (2) appropriate folding of the molecule during the dialysis period. Accurate comparisons were assured by dissolution of the NIDDK standard in 50 mM NH$_4$HCO$_3$ and the use of this to produce both the bioassay stock and the standard curve in the NanoOrange protein assay.

NIDDK PRL is extracted from pituitaries and contains a mixture of nonphosphorylated and phosphorylated forms of the hormone in addition to at least one glycosylated form. As phosphorylated PRL acts as an antagonist to nonphosphorylated PRL in the Nb2 bioassay, its presence reduces the Nb2 response. In addition, glycosylated PRL has been shown to have about one third to one fourth the biological activity of unmodified PRL, and the B3 preparation contains about 25% glycosylated PRL. Recombinant wild-type hormone produced in E. coli, by contrast, and hence a larger proliferative response to a recombinant preparation can be obtained.

Some of the increased activity is probably due to the absence of phosphorylated hormone in the recombinant wild-type PRL. For this experiment, a similar preparation of human pituitary PRL, hPRL I-8, which has less than 10% phosphorylated hormone, was subjected to dephosphorylation by acid phosphatase. Dephosphorylation of the I-8 preparation increased its ability to stimulate the proliferation of Nb2 cells. Assay of enzyme alone showed no ability to stimulate Nb2 cell proliferation.

Glutamate and Aspartate Mutants

Substitution of serine 179 with either aspartate or glutamate produced a molecule that acted as an antagonist. When either was titrated against the wild-type recombinant, a dose-related inhibition of proliferation versus wild-type PRL alone was observed. The aspartate mutant was a more potent antagonist than the glutamate mutant, as shown by FIG. 3, in that 200 pg/ml aspartate mutant inhibited the growth response to 400 pg/ml wild-type PRL by 75%.

When tested alone for intrinsic agonist activity, neither the aspartate nor the glutamate mutant showed any ability to stimulate Nb2 cell proliferation.

In summary, molecular mimics of phosphorylated PRL where a particular serine is substituted maintain the antagonist properties of the phosphorylated hormone. These pseudophosphorylated PRLs can now be used to study many aspects of the physiology of PRL, and have the potential to be useful therapeutics.

It is to be understood that while the invention has been described above in conjunction with preferred specific embodiments, the description and examples are intended to illustrate and not limit the scope of the invention, which is defined by the scope of the appended claims.

What is claimed is:

1. A recombinant nucleotide construct composed of the sequence of SEQ ID NO:1 encoding a mutated human prolactin, wherein the expression of the sequence results in a mimic of a phosphorylated human prolactin, the mimic being capable of antagonizing growth promoting effects of non-phosphorylated human prolactin, the mimic being mutated by an aspartate or glutamate residue substitution at serine 179.

2. The nucleotide sequence as in claim 1 wherein the serine is mutated by a glutamate residue substitution.

3. The nucleotide sequence as in claim 1 wherein the serine mutation is by an aspartate residue substitution.

4. A construct comprising the nucleotide of claim 2 or 3 operatively linked with an expression vector.

5. The construct as in claim 4 wherein the expression vector is mammalian, viral or bacterial.

6. A composition comprising:

a human phosphorylated prolactin mimic, the mimic in an amount effective to antagonize growth promoting effects of non-phosophorylated human prolactin, the mimic being expressible by SEQ ID NO:1, being mutated at serine 179 and being substantially free of non-phosphorylated human prolactin; and a pharmaceutically suitable carrier in which the mimic is admixed.

7. The composition as in claim 6 wherein the serine 179 is substituted by an aspartate or glutamate residue.

8. The composition as in claim 6 wherein the serine 179 is substituted by an aspartate residue.

* * * * *

SEQUENCE LISTING

<160> NUMBER OF SEQ ID NOS: 6

<210> SEQ ID NO 1
<211> LENGTH: 832
<212> TYPE: DNA
<213> ORGANISM: Homo sapiens
<220> FEATURE:
<221> NAME/KEY: mutation
<222> LOCATION: (622)...(624)
<223> OTHER INFORMATION: This is the codon for the substituted amino
      acids of the mutated sequence.

<400> SEQUENCE: 1

-continued

```
aacatgaaca tcaaaggatc gccatggaaa gggtccctcc tgctgctgct ggtgtcaaac    60
ctgctgctgt gccagagcgt ggcccccttg cccatctgtc ccggcggggc tgcccgatgc   120
caggtgaccc ttcgagacct gttttgaccgc gccgtcgtcc tgtcccacta catccataac   180
ctctcctcag aaatgttcag cgaattcgat aaacggtata cccatggccg ggggttcatt   240
accaaggcca tcaacagctg ccacacttct tcccttgcca cccccgaaga caaggagcaa   300
gcccaacaga tgaatcaaaa agactttctg agcctgatag tcagcatatt gcgatcctgg   360
aatgagcctc tgtatcatct ggtcacggaa gtacgtggta tgcaagaagc cccggaggct   420
atcctatcca aagctgtaga gattgaggag caaaccaaac ggcttctaga gggcatggag   480
ctgatagtca gccaggttca tcctgaaacc aaagaaaatg agatctaccc tgtctggtcg   540
ggacttccat ccctgcagat ggctgatgaa gagtctcgcc tttctgctta ttataacctg   600
ctccactgcc tacgcaggga tnnncataaa atcgacaatt atctcaagct cctgaagtgc   660
cgaatcatcc acaacaacaa ctgctaagcc cacatccatt tcatctattt ctgagaaggt   720
ccttaatgat ccgttccatt gcaagcttct tttagttgta tctcttttga atccatgctt   780
gggtgtaaca ggtctcctct taaaaaataa aaactgactc gttagagaca tc          832
```

<210> SEQ ID NO 2
<211> LENGTH: 228
<212> TYPE: PRT
<213> ORGANISM: Homo sapiens
<220> FEATURE:
<221> NAME/KEY: VARIANT
<222> LOCATION: 208
<223> OTHER INFORMATION: Site mutated amino acid residue where the
      normal codon coding for serine is modified preferably to encode
      for aspartate or glutamate, most preferably aspartate.

<400> SEQUENCE: 2

```
Asn Met Asn Ile Lys Gly Ser Pro Trp Lys Gly Ser Leu Leu Leu Leu
 1               5                  10                  15

Leu Val Ser Asn Leu Leu Leu Cys Gln Ser Val Ala Pro Leu Pro Ile
            20                  25                  30

Cys Pro Gly Gly Ala Ala Arg Cys Gln Val Thr Leu Arg Asp Leu Phe
        35                  40                  45

Asp Arg Ala Val Val Leu Ser His Tyr Ile His Asn Leu Ser Ser Glu
 50                  55                  60

Met Phe Ser Glu Phe Asp Lys Arg Tyr Thr His Gly Arg Gly Phe Ile
 65                  70                  75                  80

Thr Lys Ala Ile Asn Ser Cys His Thr Ser Ser Leu Ala Thr Pro Glu
            85                  90                  95

Asp Lys Glu Gln Ala Gln Gln Met Asn Gln Lys Asp Phe Leu Ser Leu
        100                 105                 110

Ile Val Ser Ile Leu Arg Ser Trp Asn Glu Pro Leu Tyr His Leu Val
    115                 120                 125

Thr Glu Val Arg Gly Met Gln Glu Ala Pro Glu Ala Ile Leu Ser Lys
130                 135                 140

Ala Val Glu Ile Glu Glu Gln Thr Lys Arg Leu Leu Glu Gly Met Glu
145                 150                 155                 160

Leu Ile Val Ser Gln Val His Pro Glu Thr Lys Glu Asn Glu Ile Tyr
                165                 170                 175

Pro Val Trp Ser Gly Leu Pro Ser Leu Gln Met Ala Asp Glu Glu Ser
            180                 185                 190

Arg Leu Ser Ala Tyr Tyr Asn Leu Leu His Cys Leu Arg Arg Asp Xaa
```

-continued

```
                    195                 200                 205
His Lys Ile Asp Asn Tyr Leu Lys Leu Leu Lys Cys Arg Ile Ile His
    210                 215                 220

Asn Asn Asn Cys
225

<210> SEQ ID NO 3
<211> LENGTH: 23
<212> TYPE: DNA
<213> ORGANISM: Artificial Sequence
<220> FEATURE:
<223> OTHER INFORMATION: This sequence is a primer.

<400> SEQUENCE: 3
gcagggatga ccacaaggtt gac                                          23

<210> SEQ ID NO 4
<211> LENGTH: 24
<212> TYPE: DNA
<213> ORGANISM: Artificial Sequence
<220> FEATURE:
<223> OTHER INFORMATION: This sequence is a primer.
<220> FEATURE:
<221> NAME/KEY: variation
<222> LOCATION: 12
<223> OTHER INFORMATION: This is a nucleic acid residue that can be
      replaced for nucleic acid substitutes.

<400> SEQUENCE: 4
cgcaagggat gnacacaagg ttga                                         24

<210> SEQ ID NO 5
<211> LENGTH: 22
<212> TYPE: DNA
<213> ORGANISM: Artificial Sequence
<220> FEATURE:
<223> OTHER INFORMATION: This sequence is a primer.
<220> FEATURE:
<221> NAME/KEY: variation
<222> LOCATION: 12
<223> OTHER INFORMATION: This is a nucleic acid residue that can be
      replaced for nucleic acid substitutes.

<400> SEQUENCE: 5
acgcagggat gnkataaaat cg                                           22

<210> SEQ ID NO 6
<211> LENGTH: 26
<212> TYPE: DNA
<213> ORGANISM: Artificial Sequence
<220> FEATURE:
<223> OTHER INFORMATION: This sequence is a primer.

<400> SEQUENCE: 6
cgtggccccc atatgttgcc catctg                                       26
```